United States Patent
Brown et al.

(10) Patent No.: US 7,273,184 B2
(45) Date of Patent: Sep. 25, 2007

(54) DISPOSABLE AIR TREATMENT DEVICE

(75) Inventors: Colin Brown, Bracknell (GB); Kishen Gohil, New Malden (GB); Guy Edward Naish, Bicester (GB)

(73) Assignee: Givaudan SA, Vernier (CH)

( * ) Notice: Subject to any disclaimer, the term of this patent is extended or adjusted under 35 U.S.C. 154(b) by 258 days.

(21) Appl. No.: 10/510,723

(22) PCT Filed: Apr. 15, 2003

(86) PCT No.: PCT/CH03/00255

§ 371 (c)(1),
(2), (4) Date: Mar. 15, 2005

(87) PCT Pub. No.: WO03/086489

PCT Pub. Date: Oct. 23, 2003

(65) Prior Publication Data

US 2005/0150973 A1    Jul. 14, 2005

(51) Int. Cl.
*A61L 9/04* (2006.01)
(52) U.S. Cl. .............. 239/6; 239/56; 239/57; 239/58; 220/87.1

(58) Field of Classification Search .......... 239/6, 239/34, 53, 54, 56, 57, 58, 59; 220/87.1; 422/5, 305
See application file for complete search history.

(56) References Cited

U.S. PATENT DOCUMENTS

| | | | | |
|---|---|---|---|---|
| 1,931,132 A | * | 10/1933 | Hinckley | .............. 220/87.1 |
| 3,840,145 A | * | 10/1974 | Almanza | .............. 220/87.1 |
| 3,955,706 A | * | 5/1976 | Whitaker | .............. 239/55 |
| 4,279,373 A | | 7/1981 | Montealegre | |
| 4,549,693 A | | 10/1985 | Barlics | |
| 5,492,675 A | | 2/1996 | Brizard | |
| 5,988,520 A | * | 11/1999 | Bitner | .............. 239/6 |

FOREIGN PATENT DOCUMENTS

| | | |
|---|---|---|
| DE | 32 39 511 A | 4/1984 |
| GB | 492 169 A | 9/1938 |
| WO | WO 95 19305 A | 7/1995 |

* cited by examiner

Primary Examiner—Steven J. Ganey
(74) *Attorney, Agent, or Firm*—Christa Hildebrand; Norris McLaughlin & Marcus, PA

(57) ABSTRACT

A disposable air treatment device that can be hung on the rim of a garbage bin which comprises a hanger component adapted to secure the air treatment device to a garbage bin, and a volatile material dispenser adapted to dispense a volatile material to the interior.

8 Claims, 7 Drawing Sheets

DISPOSABLE AIR TREATMENT DEVICE

This invention relates to the avoidance or masking of unpleasant odours in garbage bins.

Garbage bins for the deposition of rubbish come in a variety of shapes, sizes and configurations. A typical home or office will have several, and these may vary from small pedal bins wherein depression of a foot pedal tips up a covering lid which otherwise covers the interior of the bin which contains the garbage, to medium sized swing-lid bins which have a cover with a swinging cover or plate which is moved to insert garbage into the interior of the bin which contains the garbage, to large outdoor refuse cans or garbage cans which may have hinged, or unhinged lids which cover the interior of the cans which contain the garbage. In many cases, the bins used indoors are used in conjunction with liner bags. These liner bags serve a dual function of both allowing convenient disposal of garbage and also keeping the bin relatively clean.

A major problem with any bin into which waste food or other organic material is placed is that decay of the organic material rapidly generates a malodour that fills the headspace of the bin (that part of the bin unfilled with garbage), especially in the case of lidded bins. As the lid of the bin is opened, this malodour is released. One traditional method to remedy this involves the spraying of air fresheners into the bin. This, however, only has an immediate or short-term effect and over time the malodour returns. Another traditional method is to provide a powdered or granular air freshener or odour counteractant in order to combat malodours. However, after such a treatment, any subsequent treatment of the garbage will cover the powder and the overlaying organic material will still create malodour in the head space.

Various approaches have been tried and even commercialized, but none has yet succeeded in providing a completely satisfactory approach. The ideal product is one that that can be positioned at the top of the bin, where it delivers fragrance and/or odour counteractant into the head space of the bin. For best performance, the device should be attached in such a way that garbage entering the bin cannot dislodge it and fluid material entering the bin cannot block the evaporative surface. It is also desirable that the use of the device involve the minimum of handling by the user. It should also be usable with and without liner bags The present invention provides an improved disposable air treatment device that is particularly adapted for use with garbage bins, which garbage bins may be used with or without a liner bag, which devices are particularly efficacious in controlling malodours in the headspace of garbage bins. The disposable air treatment device according to the invention is adapted to hang over the rim of a garbage bin in which it is used, and to deliver in the span of a few days, generally between 0-7 days, a volatile material to the headspace of a garbage bin, said volatile material desirably being at least one of: a fragrancing material, an odour masking material, and an insect controlling material. The invention therefore provides an air treatment device adapted to be used on a garbage bin, which comprises: a hanger component adapted to secure the air treatment device to a garbage bin, and a volatile material dispenser adapted to dispense a volatile material to the interior of a garbage bin.

By "hanger component" is meant any convenient means of hanging a volatile material dispenser within a garbage bin. A variety of ways are described hereinunder with reference to the drawings, but it will be understood that these are only exemplary and that there are many others that are not described, but that fall within the scope of the invention.

The design of the improved disposable air treatment device is such that it is resistant to being prematurely dislodged into the garbage bin in which it is used. Preferred embodiments of the improved disposable air treatment device are ones that can be manufactured from low cost materials such that the device, while being effective, is not too costly to be of a single-use type, and thus disposable. The air freshener device may be conveniently dropped into the liner bag as it is removed from the garbage bin, or alternatively, it may be disengaged from the rim of the garbage bin as the garbage bin is emptied in the instance where no liner bag is used. It is also envisaged that, each time a new bag is placed in the garbage bin or the garbage bin is emptied, a new device according to the invention would be hung over the rim. It is envisaged that the device would be cheap and simple enough to allow its sale in multiple packs for the equivalent price of a normal large area air freshener.

The volatile materials which may be used in conjunction with any of the disposable air treatment devices taught herein may be any volatile or evaporable material, but is desirably one or more materials which have a cosmetic effect such as a fragrancing or odour masking effect, an insecticidal effect or a medical effect. They may be liquid compositions. They may be in the form of pure oils, such as pure essential oils, but more commonly they are in the form of mixtures of constituents, which may include water, to form aqueous compositions. The materials can be relatively simple in composition, or they can be a complex mixture of natural and/or synthetic chemical components, and any material which may be volatilized and dispensed by the use of the present invention may be used. Fragrance can be a synthetically formed material, or a naturally-derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin and Neroli, Rose absolute.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odours, such as lime, lemon or orange.

Additionally, a wide variety of chemicals is known for fragrancing, air freshening, odour masking, insect controlling or other effect. These include aldehydes, ketones, esters, alcohols, terpenes. Synthetic types of fragrance compositions either alone or in combination with natural oils may also be used. Synthetic liquid fragrance compositions include, inter alia, geraniol, geranyl acetate, eugenol, isoeugenol, linalool, linalyl acetate, phenethyl alcohol, methyl ethyl ketone, methylionone and isobornyl acetate. Other materials useful in fragrancing, air freshening and odour masking may also be used in the present invention. As noted above, the volatile air treatment material according to the invention may also be a formulation, such as a liquid formulation containing an insect repellent material, such as citronellal. Additionally the volatile air treatment material according to the invention may also be a formulation directed to provide a beneficial therapeutic effect, such as eucalyptus or menthol.

Such volatile materials may be presently commercially obtained from a variety of sources and from a variety of suppliers including: Givaudan Corp. (Teaneck, N.J.); Berje Inc. (Bloomfield, N.J.); BBA Aroma Chemical Div. of Union Camp Corp. (Wayne, N.J.); Firmenich Inc. (Plainsboro N.J.); Quest International Fragrances Inc. (Mt. Olive Township, N.J.); Robertet Fragrances Inc. (Oakland, N.J.), or from other suppliers not necessarily listed herein.

The invention is now further described with reference to the drawings, which depict preferred embodiments and are not to be considered to limit the invention in any way.

Figure 1A:
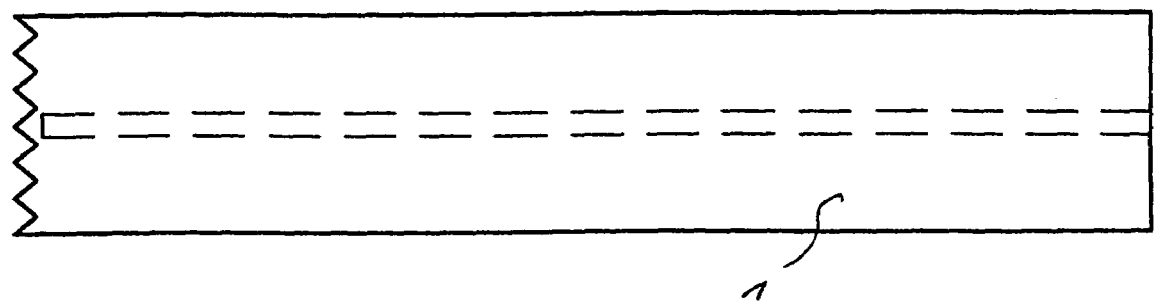
FIGS. 1A and 1B depict respectively a plan view and a transverse cross-section of a first hanger component according to the invention.
Figure 1B:
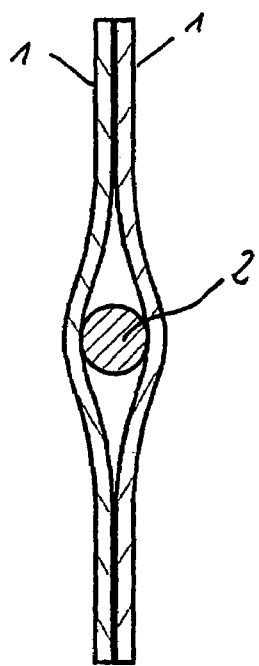
Figure 11:
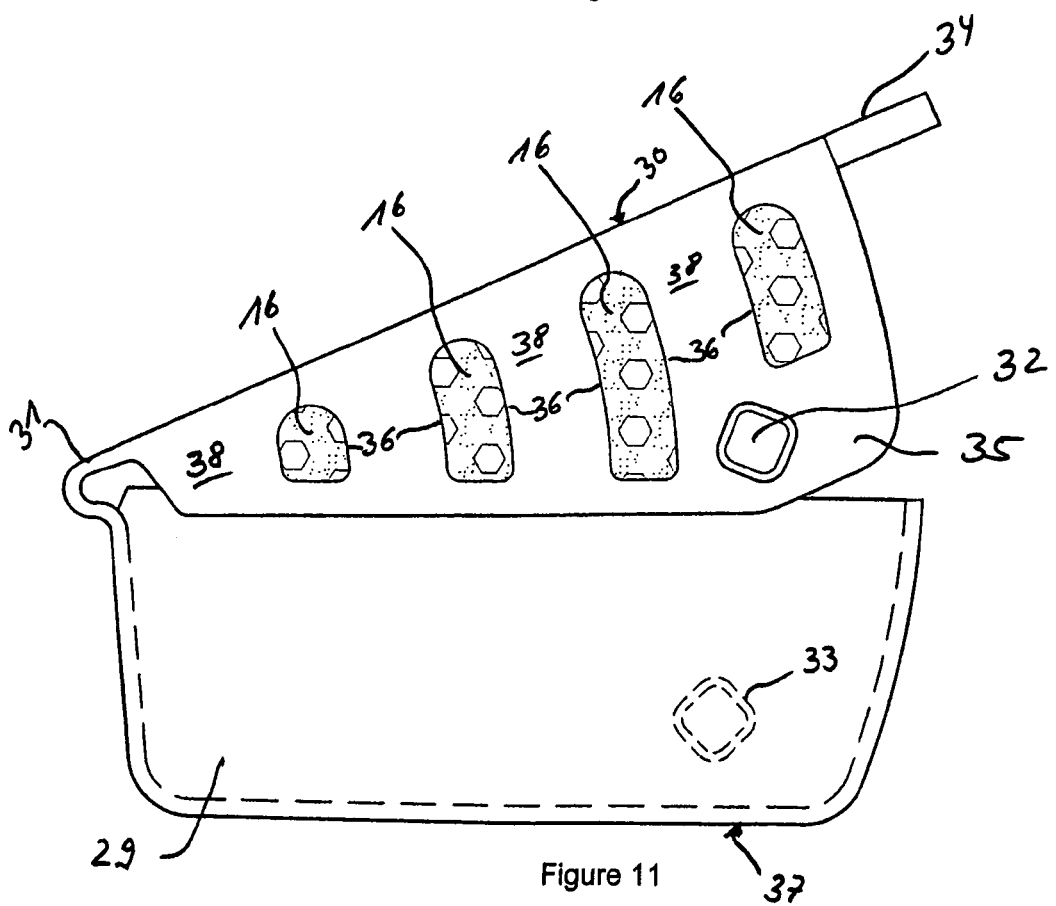

FIG. 11 depicts a still further volatile material dispenser according to the invention A first embodiment of a hanger component is a tab 1 as depicted in FIGS. 1A and 1B. Illustrated is a simple elongated tab 1 composed of two strips of thin flexible material such as paper, cardboard, fabric or plastic, adhered together, with a metal wire 2 being held between them. This tab could also be a single sheet of material with the wire adhered to one. It is also envisaged that there may be two or more wires, which are used in the tab 1. It is also envisaged that the tab could be composed of only a length of wire 2 without the additional tab material 1 or the tab 1 may be a loop of wire, which may either be coated or bare. When present, the diameter of the wire 2 is not critical to the invention, but is preferably less than 1 mm and most preferably between about 0.1-0.9 mm, so that it is bendable to fit the rim of a garbage bin. The wire 2 should be of a material and type that, when bent, retains the shape into which it has been bent, and it should be thick enough so that, when the tab 1 is bent, the wire 2 can overcome any natural tendency of the material of the tab 1 to spring back into shape. Alternatively, the tab 1 may be formed of a flexible, shape-retaining material, such that, when it is bent from a flat configuration, it can be formed to grasp or hang upon the rim (or other part) of a garbage bin. Exemplary flexible, shape-retaining materials include metallic foils or strips, coated metallic foils or strips, as well as laminates of metallic foils or strips with one or more further materials such as paper, polymer films, as well as textiles or fabrics. In use, at least a part of this tab 1, of whatever form, is bent over a rim (or other part) of a garbage bin in such a way that volatile material dispensing component of the device (not shown in FIG. 1) would be held within the headspace of the garbage bin.

Figure 2A:
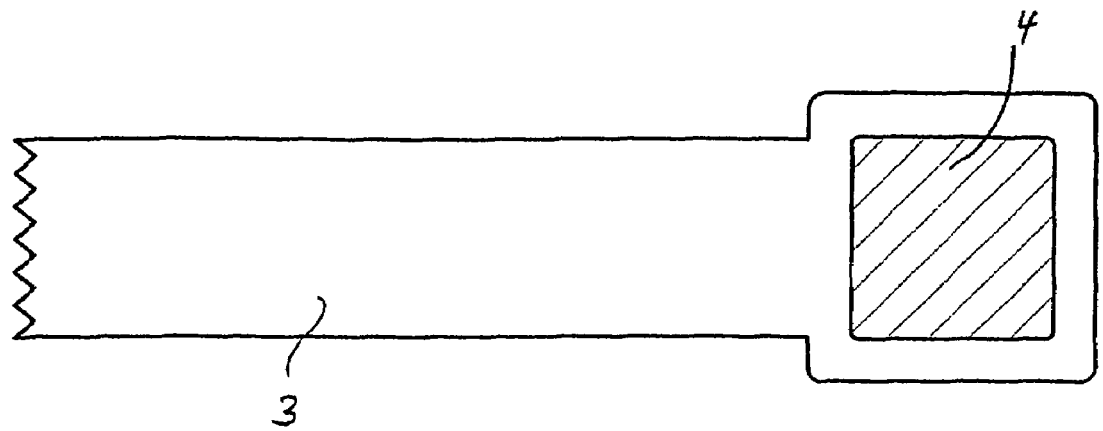
FIGS. 2A and 2B depict respectively a plan view and a transverse cross-section of a second hanger component according to the invention.
Figure 2B:
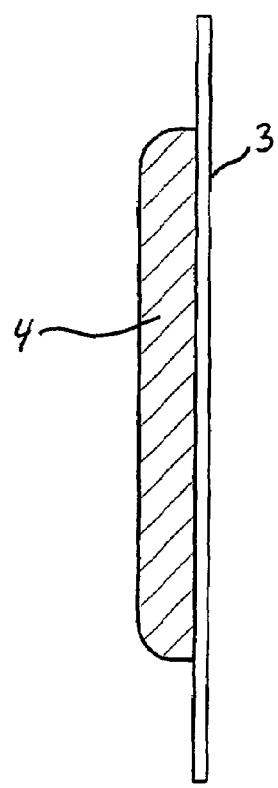

FIGS. 2A and 2B illustrate an alternative embodiment of a hanger component according to the invention. Depicted is an elongated tab 3 having a pad 4. On one side of the pad 4 is disposed an adhesive which may optionally be protected by a peelable strip (not shown). In use, the peelable strip (if present) would be removed and the pad 4 adhered to either the outside of the garbage bin and the elongated tab 3 bent over into the interior of the garbage bin so that volatile material dispending component of the device (not shown) would be held within the headspace of the garbage bin. Alternatively, where a bin liner is used, the peelable strip (if present) would be removed and the pad 4 adhered to the bin liner, preferably on that portion of the bin liner that is folded over the rim of a garbage bin, which portion is on the exterior of the garbage bin. In such an embodiment, the preferred adhesives used would be of a type that would allow the pad 4 to be easily removed without tearing the bin liner, or when such hanger component is used without a bin liner, would be an adhesive of the type that would not leave an unwanted residue on the surface of the garbage bin. The elongated tab 3 may be formed of the same types of flexible, shape retaining materials include metallic foils or strips, coated metallic foils or strips, laminates of metallic foils or strips, paper, polymer films, as well as textiles or fabrics useful in the manufacture of tab 1 according to FIG. 1, but need not be flexible or be a shape retaining material as the adhesive facilitates in the retention of the inventive device with respect to the garbage bin.

Figure 3:
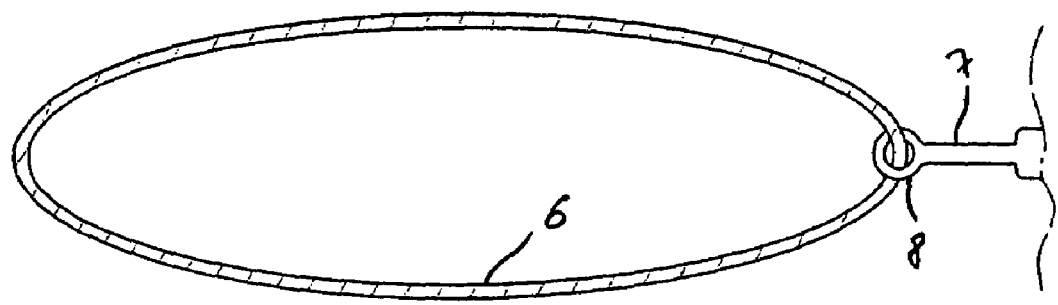
FIG. 3 depicts a perspective view of a third hanger component according to the invention.

A still further alternative embodiment of a hanger component according to the invention is depicted in FIG. 3. There is illustrated an elastic ring 6 onto which is hung a tab 7 by a loop 8. In use, the elastic ring 6 is stretched about a part of the garbage bin, especially the periphery of the rim so that the tab 7, and the volatile material dispensing component (not shown) depending from or affixed to the tab 7 is suspended within the interior of the garbage bin, particularly in the headspace thereof. The tab 7 itself may be made of any suitable material, including the materials of which the elongated tab 3 of FIG. 2 may be produced. The elastic ring may be formed of any suitable elastic material, such as an elastomer, e.g. natural or synthetic rubber. Further, while a loop 8 is depicted, any other element or technique may be used to affix the elastic ring 6 to the tab 7 such as a hook, or by passing a part of the elastic ring 6 through a perforation included in the tab 7.

Figure 4:
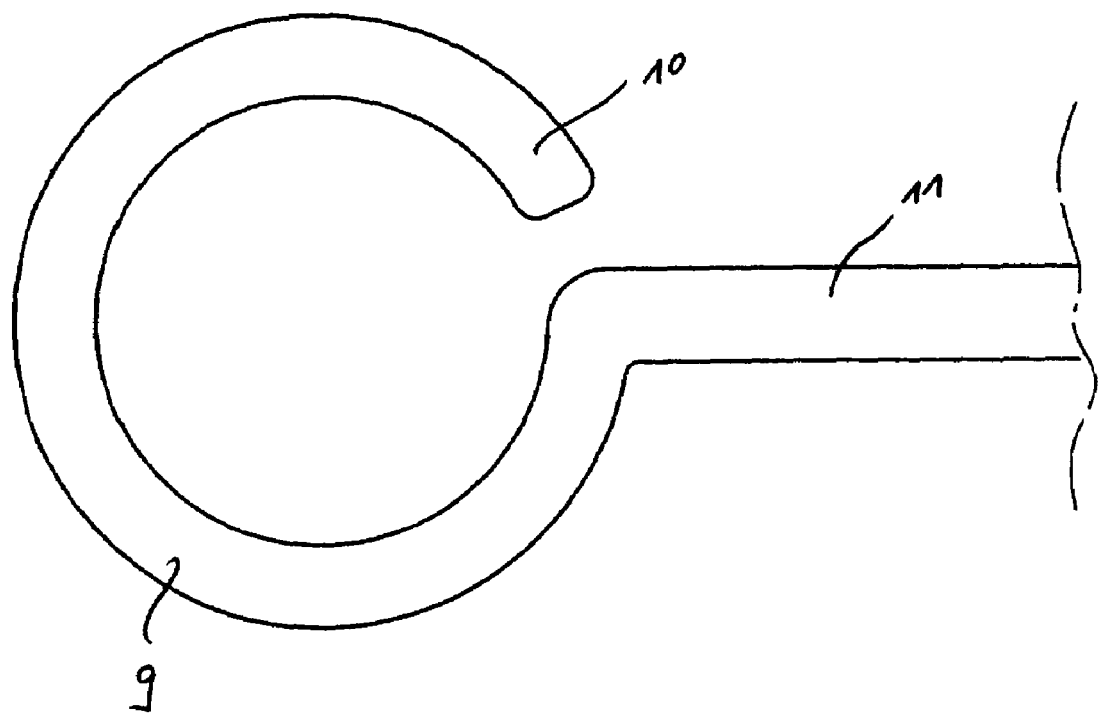
FIG. 4 depicts a fourth hanger component according to the invention.

FIG. 4 illustrates in detail a looped hook 9 which may be used as a hanger component of the invention. FIG. 4 shows a looped hook 9 having an end 10 and a shaft 11. In use the end of the looped hook 9 can be positioned on the rim (or other part) of the garbage bin, such that the volatile material dispensing component (not shown) depending from or affixed to the hook 10 via the shaft 11 is suspended within the interior of the garbage bin, particularly in the headspace thereof. The looped hook 9 may be made of any suitable material, such as those useful for producing the flexible tab 1 of FIG. 1, or the elongated tab 3 of FIG. 2. The looped hook 9 may be flexible or inflexible The second component of the invention is a volatile material dispenser is adapted to dispense a volatile material to the interior of a garbage bin, particularly to the headspace thereof.

Figure 5:
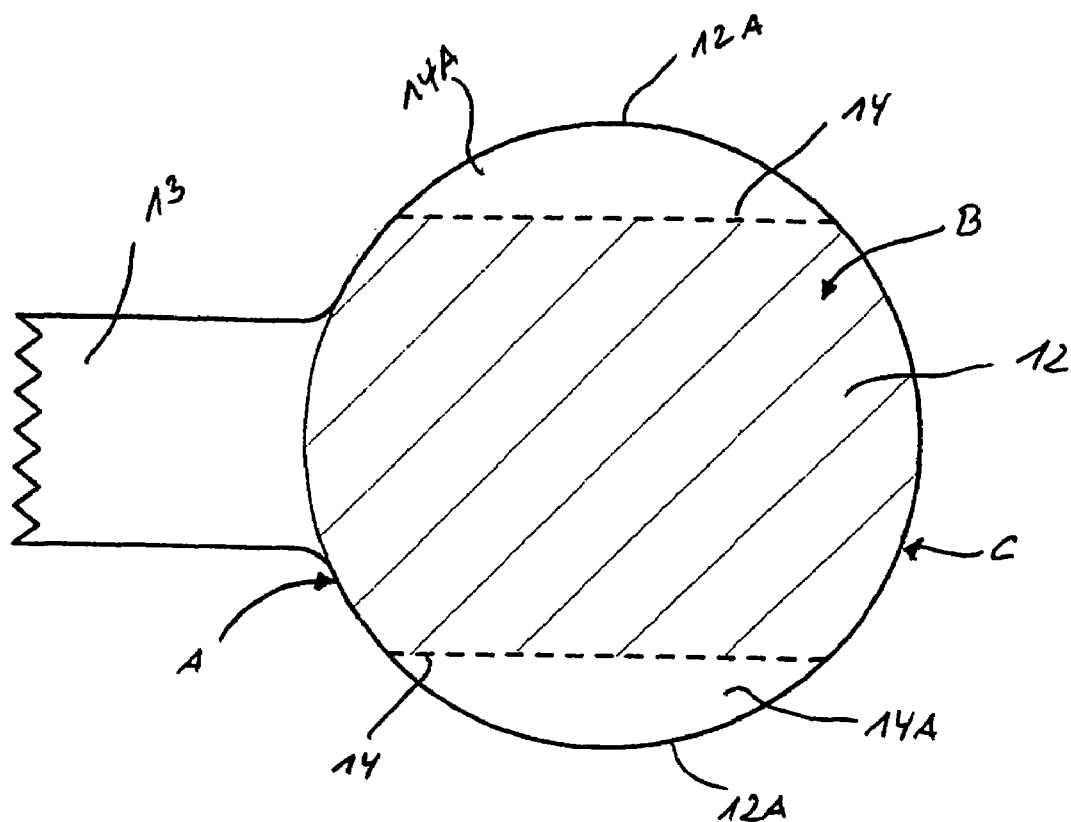
FIG. 5 depicts a volatile material dispenser according to the invention.

FIG. 5 shows a first embodiment of a volatile material dispenser according to the invention. As depicted, the volatile material dispenser is a simple, generally planar support element A, here disc-shaped, and having two opposite faces, face B which is visible in FIG. 5, and face C which is on the reverse side of the disc-shaped element A but not visible in FIG. 5. The support element A may be formed of an absorbent material in which case faces B and C would be evaporative surfaces, or alternatively the support element A may be formed of a non-absorbent material, but have affixed to face B and/or face C an absorbent material which would provide an evaporative surface. Such an evaporative surface 12 is depicted in FIG. 5. The evaporative surface(s) may cover the total area of faces B and/or C of the support element A but need not be, as shown in FIG. 5 where the surface area of the evaporative surface 12 is less than the surface area of face B as depicted by the region of hatched lines. Although not shown in particular detail in FIG. 5, it is to be understood that the volatile material dispenser, here the support element A comprising an absorbent material, is attached to a hanger component 13, which could be any hanger component, especially one or more of the hanger components discussed with reference to any of FIGS. 1, 2, 3 and 4, which however is not shown in FIG. 5.

The volatile material dispenser according to FIG. 5 could first be manufactured and thereafter a volatile material would be supplied to the evaporative surface(s) of the device. Such would be by any suitable means, including conventional means of soaking, spraying or otherwise impregnating the evaporative surface(s) with a volatile material prior to its use. Subsequent to its manufacture, and during transport to an ultimate consumer, the whole volatile material dispenser could be stored in a pouch or bag of non-porous material, such that the volatile material would only be released when pouch or bag were breached, and the device removed, after which the pouch or bag would typically be discarded. Such would be convenient where the support element A is formed of an absorbent material. Alternatively, where the support element A is formed of a non-porous material, upon which was affixed a pad or formed sheet of an absorbent material as the evaporative surface 12, it is also contemplated that a non-porous cover sheet or film could be attached to sandwich the impregnated evaporative surface between support element A and the non-porous cover sheet or film. A suitable adhesive could be interposed between contacting portions of the support element A and non-porous cover sheet or film. In such an arrangement the impregnated evaporative surface 12 would be disposed between the surfaces of two non-porous elements which would provide a barrier to the premature volatilization of the volatile material. In use, the consumer would need only to peel off the non-porous cover sheet or film and then hang the volatile material dispenser within a garbage bin. The advantage of this latter configuration is that no pouch or bag would be needed, or need to be discarded.

It is contemplated that a number of variations to a volatile material dispenser according to FIG. 5 may be provided and yet clearly fall within the scope of the present inventive teaching. One such variation is in the provision of support elements A having geometries other than the simple, generally planar disc-shape illustrated in FIG. 5, particularly different two-dimensional shapes or three-dimensional shapes. A further optional variation is that the support element A may include score lines or perforations defining fold marks 14 which could be conveniently bent so to convert the support element A from a generally planar, two-dimensional shape into a three-dimensional shape. According to such a configuration, as is shown on FIG. 5, the portions 14A of the support element A between the periphery 12A of the evaporative surface 12 and the fold marks 14 would desirably be bent in the same direction and extend outward from the evaporative surface 12 thus imparting a three-dimensional shape to the volatile material dispenser depicted on FIG. 5. Thereafter the volatile material dispenser could be provided to the interior of a garbage bin such that at least part of one evaporative surface 12 would not contact the inner wall of the garbage bin or bag liner. By way of illustration and with reference to FIG. 5, the portions 14A of the support element A between the periphery 12A of the evaporative surface 12 may be bent upward out of the plane defined by the evaporative element 12, and thereafter the volatile material dispenser could be provided to the interior of a garbage bin such that the evaporative surface 12 would face the inner wall of the garbage bin or bag liner, with the bent portions 14A functioning as buttresses between the inner wall of the garbage bin or bag liner and the evaporative element 12. Such a configuration of the volatile material dispenser and its installation in a garbage bin would result in a protected evaporative surface facing the interior wall of the garbage bin that would continue to emanate fragrance and odour counteractant even if one face of support element A was contaminated with garbage.

Figure 6:
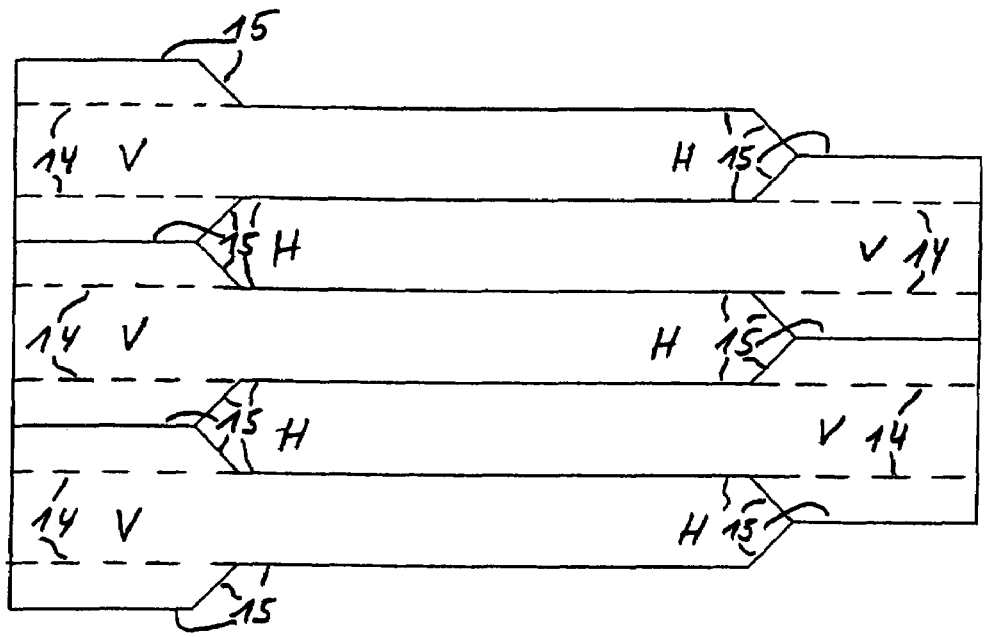
FIG. 6 depicts a layout of volatile material dispensers formed from a sheet.

FIG. 6 depicts a layout and method for the manufacture of an embodiment of an improved disposable air treatment device according to the invention from a sheet of absorbent material in such a way as to minimize waste from the sheet. Each of the solid lines 15 in FIG. 6 represent cut lines, which also define the form of a disposable air treatment device according to the invention, each including a hanger component H, and a volatile material dispenser component V. Although only four such disposable air treatment devices are depicted on FIG. 6 it is to be understood that the pattern defined by the solid lines 15 may be repeated as desired. Optionally the hanger component H may be used as is, or modified as desired so that it may appropriately fulfill its function. Preferably the hanger component H may be modified so to conform with one or more of the embodiments of hanger components described with reference to FIGS. 1, 2, 3 or 4. The volatile material dispenser component V may also be modified, if desired so to conform it with one or more of the embodiments described and discussed in reference to FIG. 5. For example, the volatile material dispenser component V may optionally be provided with perforations or score lines 14 as depicted in FIG. 5 which are used to facilitate the folding of the absorbent sheet from which the improved disposable air treatment device according to the invention are made.

It is contemplated that a number of variations to the layout and method for the manufacture of an embodiment of the improved disposable air treatment device according to FIG. 5 may be provided and yet clearly fall within the scope of the present inventive teaching. For example the sheet need not be an absorbent sheet and may be a sheet of a nonporous material, in which instance pads, sheets or other elements formed of an absorbent material need be applied to each device in order to function as the volatile material dispenser component of the invention. Such may be applied to one or both sides of the nonporous sheet and desirably in the region V.

Figure 7:
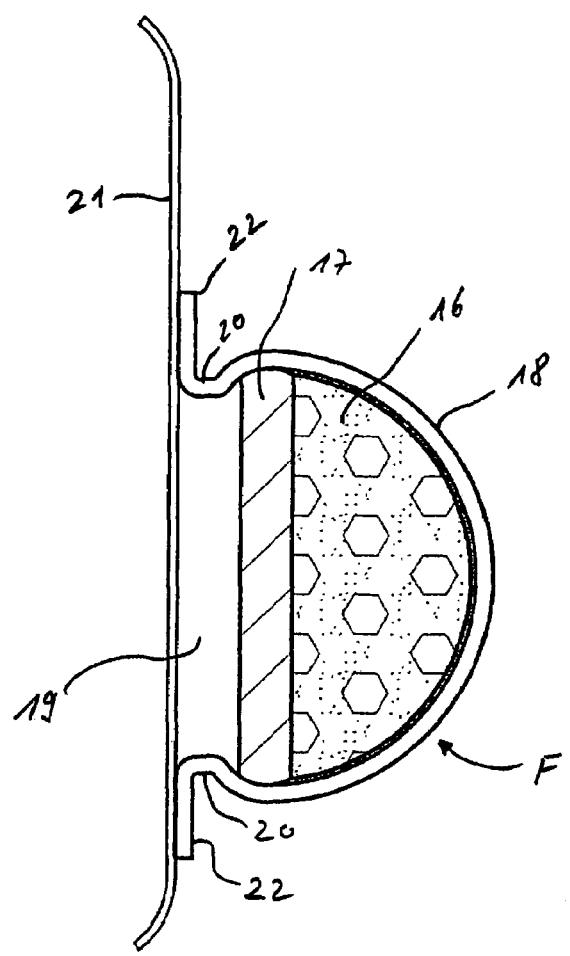
FIG. 7 depicts a cros-section of a second volatile material dispenser according to the invention.

FIG. 7 depicts a cross-sectional view of a further alternative embodiment of a volatile material dispenser according to the invention, which includes a container 18 of a non-porous material defining a cavity containing an absorbent material 16 within the cavity and a porous retaining member 17. This porous retaining member 17 functions to prevent the absorbent material 16 from exiting the cavity but to permit for the passage of volatile material entrained or absorbed by the absorbent material therethrough. The porous retaining member 17 may be any suitable porous member but is conveniently a solid sheet of a porous material such as plastic, paper, cardboard, textile or other fibrous or porous material, or alternatively it may be a perforated sheet of a non-porous material. The porous retaining member 17 is conveniently retained by one or more constrictions 20 present within the container 18. These constrictions 20 may take the form of one or more discrete elements or may be a single continuous construction around the inner circumference of the container. It is contemplated that the porous retaining member 17 may be omitted in certain embodiments, particularly in those wherein the absorbent material 16 is non-pulverulent and may be retained within the cavity of the container 18 by a friction fit, by an adhesive, or by being cast or formed in place, e.g., it is a gel useful in dispensing the volatile material. In a preferred embodiment, the container is molded from a non-porous material especially a single or multi-layered polymer film which may be suitably molded, especially via conventional vacuum molding or draw molding techniques. Desirably the container 18 also includes a peripheral flange 22 about an open face 19. The peripheral flange 22 provides a surface upon which a peelable non-porous barrier film 21 may be applied to close the device, during its transport and up to its use by the ultimate consumer. Such a barrier film is designed to be removed just prior to the use of the device. This volatile material dispenser may include a hanger component which is integrated into its construction; this feature is not shown in FIG. 7, but it may be selected from any suitable hanger component, for example, those shown in FIGS. 1, 2, 3, and/or 4. For example, it is envisaged that a portion of the flange 22 may include a hook to facilitate the hanging of the device F within a garbage bin.

Figure 8:
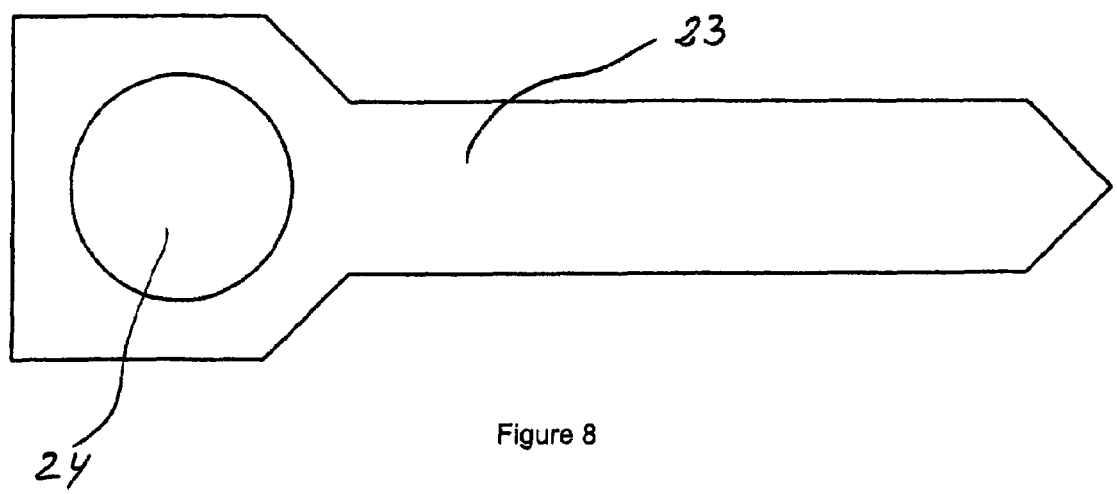
FIG. 8 depicts a hanger component particularly adapted for use with the volatile material dispenser according to FIG. 7.

FIG. 8 depicts a hanging component that may be used with the volatile material dispenser shown to FIG. 7. The hanging component of FIG. 8 includes a tab portion 23 and a perforation 24 which is suitably dimensioned to receive a portion of the container 18 shown on FIG. 7. In use the container 18 is inserted within the perforation 24 until further insertion is restricted by the flange 22, and thereafter the tab portion 23 is used to hang the device F within a garbage bin. The tab portion 23 may be in accordance with, for example, one or more of the hanging components described with reference to FIGS. 1, 2, 3 or 4.

Figure 9:
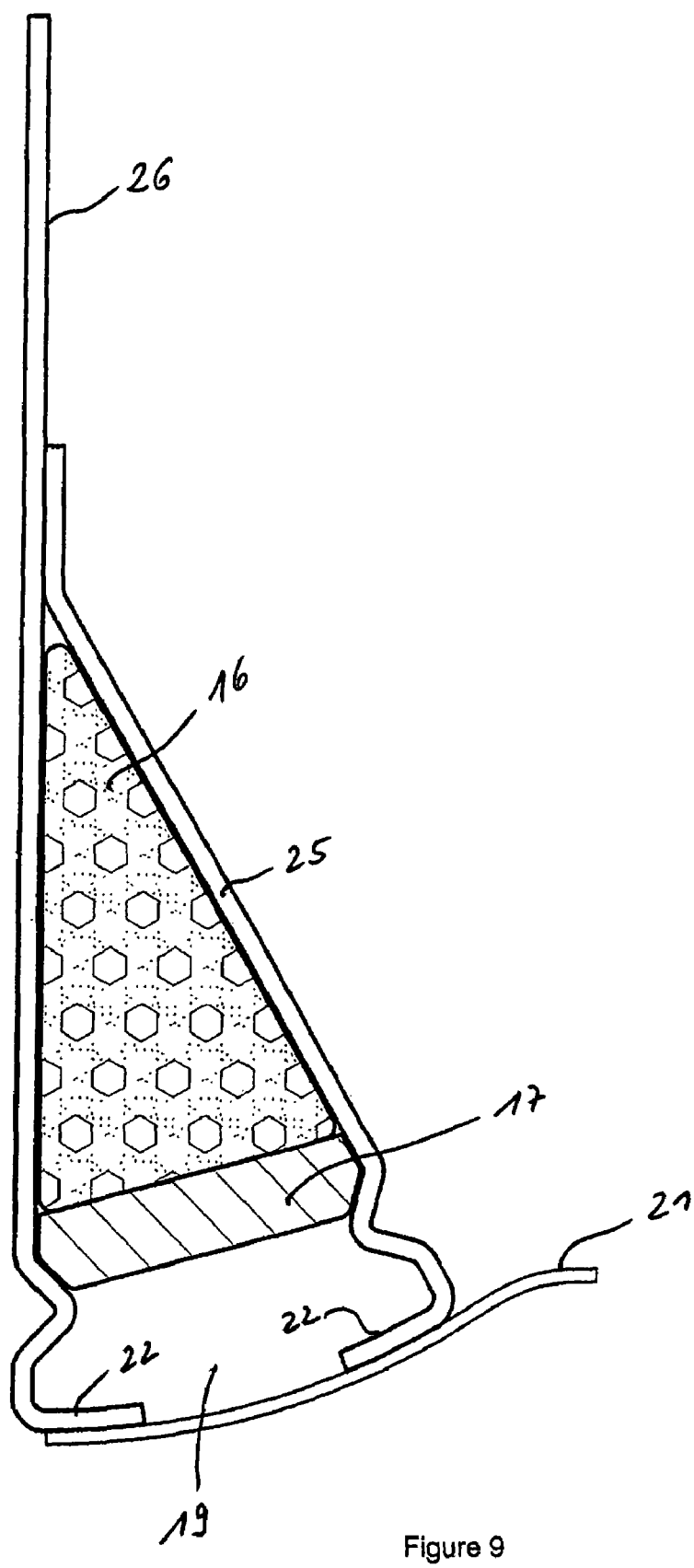
FIG. 9 depicts a cross-section of a further embodiment of a disposable air treatment device according to the invention.

FIG. 9 depicts a further embodiment of an improved disposable air treatment device, which includes a hanger component and a volatile material dispenser, which device is shaped so as to ensure that any garbage falling past it will slide or bounce off and thus not untimely defeat the functioning of the volatile material dispenser. Affixed to a hanger 26 is a cone-shaped container 25. The features and function of the cone-shaped container 25, the absorbent material 16, porous retaining member 17, constrictions 20, flange 22 and peelable non-porous barrier film 21 are the same as those of the like-numbered elements of FIG. 7, with the opening directed generally downwards towards the bottom of the interior of the garbage bin. The device according to FIG. 9 and its installation and use in such a manner provided is expected to provide that any garbage being inserted into the garbage bin will be deflected away from the device and especially from its open face 19 through which the volatile material emanates into the headspace of the garbage bin.

It will be understood that numerous variations of tab nature and container shape are possible with respect to the embodiment shown in FIG. 9, without materially altering the invention in any way. Such variations are within the scope of the invention.

Figure 10:
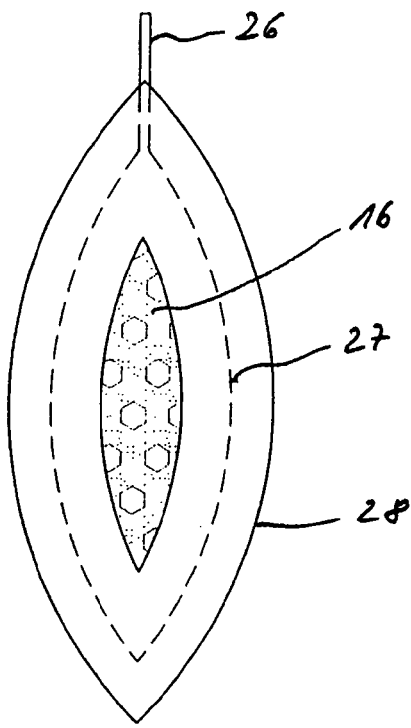
FIG. 10 depicts a further volatile material dispenser according to the invention.

FIG. 10 depicts a further embodiment of a volatile material dispenser useful in an improved disposable air treatment device according to the invention. The volatile material dispenser includes a volatile material which is entrained, absorbed or impregnated within an absorbent material 16, said absorbent material 16 being encased in a pouch 27 formed of or including a porous material such as a porous plastic, paper, cardboard, textile or other fibrous or porous material or the pouch 27 may alternately be a perforated sheet of a non-porous material. The pouch 27 is affixed to a hanger component (not shown) via element 26, preferably one or more of the hanger components described with reference to FIGS. 1, 2, 3 and/or 4 which may be used. Subsequent to its manufacture the absorbent material 16 and pouch 27 is preferably encased within a pouch or bag of a non-porous material which provides a barrier to the premature volatilization of the volatile material within the absorbent material 16. Just prior to its use, the pouch 28 is removed and discarded prior to placing the device onto the bin by the ultimate consumer.

FIG. 11 depicts a further embodiment of a volatile material dispenser according to the present invention, which includes an openable container which includes a cover shell 29 and a body 35 formed of a non-porous material which are attached by a intermediate hinge 31. In a closed position, the body 35 is inserted within the cover shell 29. The container may be moved into an open position by swinging the body 35 from within the cover shell 29 to expose sidewalls 38 (only one sidewall is shown on FIG. 11). The body 35 contains an absorbent material 16 of the type described with reference to FIGS. 7, 9 and 10 which absorbent material contains a volatile material. The body 35 itself forms a closed volume suited for containing the absorbent material, but for the provision of one or more vents 36 which permit the passage of the volatile material from the interior of the body 35 and from the absorbent material 16 through these one or more vents 36. While not depicted in FIG. 11, it is contemplated that the vents 36 may be spanned by a porous retaining member 17 which would prevent the absorbent material 16 from exiting the body 35 but at the same time permitting for the passage of volatile material from the body 35. therethrough. Once open, and in order to resist closure of the openable container the sidewalls optionally but desirably include one or more retention tabs 32 which, once they are withdrawn from within the cover shell 29 resist the reinsertion of the cover shell 29 and closing of the openable container. Optionally but again desirably the cover shell 29 includes cavities within which the retention tabs 32 fit when openable container is in a closed position. It is contemplated that the volatile material dispenser illustrated on FIG. 11 is used with a hanger component, and in particular one or more of the hanger components according to any of the embodiments according to FIGS. 1, 2, 3, and/or 4. Preferably such hanger component is affixed to the bottom surface 37 of the cover shell 29. In use, the ultimate consumer would grasp extended tab 34 to pull the body 35 outwardly from the cover shell 29 to expose at least a part of the vents 36, after which the hanger component of the device would be used to suspend the volatile material dispenser within the interior of a garbage bin. When installed and used in such a manner, it is expected that any garbage being inserted into the garbage bin will be deflected away from the device off top surface 30 and especially away from the exposed parts of vents 36 through which the volatile material emanates into the headspace of the garbage bin.

The materials of construction should be ones which permit for the manufacture of the device described herein in an effective, and low cost manner. As the non-porous materials described according to the various embodiments described herein it is contemplated that any material that provides a barrier to the volatile material may be used. By way of non-limiting example useful nonporous sheets include, e.g., coated paper, coated cardboard, coated cardstock, polymer sheets or films, multilayer polymer sheets or films, metallic foils or strips, coated metallic foils or strips, as well as laminates of metallic materials or polymer materials with one or more further materials such as paper, cardboard, cardstock, as well as other materials known to the art but not particularly elucidated here. Absorbent materials contemplated as being useful include any material that is effective as a reservoir for containment of the volatile materials discussed hererin, particularly where the volatile materials are supplied as liquids. By way of non-limiting example useful absorbent materials include fibrous materials such those from natural or synthetic sources either in woven, non-woven, twisted or bundled form, paper, cardboard, absorbent polymers, glass fibers, wool, pulvurent or non-pulvurent material, gels as well as other useful absorbent materials known to the art but not particularly elucidated here.

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

The invention claimed is:

1. An air treatment device, comprising:
   a hanger component adapted to secure the air treatment device to a garbage bin;
   a volatile material dispenser adapted to dispense a volatile material to the interior of a garbage bin, wherein the volatile material dispenser is an openable container that comprises a cover shell and an absorbent material-containing body that is enclosed within the shell and is hingeably attached thereto, such that it can be moved into an open, volatile material-emitting position, the body comprising sidewalls having vents therein, which vents are blocked when the body is within the cover shell, but which, when the body is hinged outwards from the cover shell, allows the volatile material to escape into the atmosphere.

2. An air treatment device according to claim 1, wherein the volatile material dispenser is a planar support element having two faces, at least part of one of the two faces comprises absorbent material containing volatile material, which may evaporate therefrom.

3. An air treatment device according to claim 1, wherein the volatile material dispenser is a container of a non-porous material defining an open cavity containing an absorbent material within the cavity and held therein by a porous retaining member, this porous retaining member preventing the absorbent material from exiting the cavity but permitting the passage of volatile material entrained or absorbed by the absorbent material therethrough and thus into a bin via an opening of the cavity.

4. An air treatment device according to claim 3, wherein a longitudinal cross-section of the volatile material dispenser is essentially triangular, with the base of the triangle defining the opening of the cavity and is generally downwardly pointing with respect to a bin within which it is located.

5. An air treatment device according to claim 1, wherein the volatile material dispenser is a pouch of a non-porous material containing an absorbent material, the volatile material exiting from the pouch via a porous material in the pouch, or via perforations in the pouch or part thereof.

6. A method for treating the a headspace within the interior of a garbage bin, comprising the steps of:
   providing an air treatment device according to claim 1;
   providing the volatile material dispenser to the interior of the garbage bin.

7. A method for treating the headspace within the interior of a garbage bin according to claim 6, comprising the steps of:
   delivering the volatile material to the headspace over the span of a few days;
   subsequently discarding the air treatment device in the garbage.

8. An air treatment device according to claim 1, wherein the volatile material is at least one volatile material selected from one of fragrancing material, odour masking material and insect controlling material.

* * * * *

UNITED STATES PATENT AND TRADEMARK OFFICE
CERTIFICATE OF CORRECTION

PATENT NO. : 7,273,184 B2  Page 1 of 1
APPLICATION NO. : 10/510723
DATED : September 25, 2007
INVENTOR(S) : Brown et al.

It is certified that error appears in the above-identified patent and that said Letters Patent is hereby corrected as shown below:

Column 3, line 22, "cros-section" should read -- cross section --.

Column 4, line 55, "is a volatile material dispenser is adapted" should read -- is a volatile material dispenser which is adapted --.

Signed and Sealed this

Twenty-third Day of September, 2008

JON W. DUDAS
*Director of the United States Patent and Trademark Office*